(12) United States Patent
Jäkärä et al.

(10) Patent No.: US 6,264,790 B1
(45) Date of Patent: Jul. 24, 2001

(54) PROCESS FOR THE PERACID BLEACHING OF CHELATED CHEMICAL PULP

(75) Inventors: Jukka Jäkärä, Vaasa; Aarto Paren, Valkeakoski; Reijo Aksela; Ilkka Renvall, both of Espoo, all of (FI)

(73) Assignee: Kemira Chemicals Oy, Helsinki (FI)

( * ) Notice: Subject to any disclaimer, the term of this patent is extended or adjusted under 35 U.S.C. 154(b) by 0 days.

(21) Appl. No.: 09/194,349

(22) PCT Filed: May 30, 1997

(86) PCT No.: PCT/FI97/00333

§ 371 Date: Nov. 24, 1998

§ 102(e) Date: Nov. 24, 1998

(87) PCT Pub. No.: WO97/45586

PCT Pub. Date: Dec. 4, 1997

(30) Foreign Application Priority Data

May 30, 1996 (FI) .......................................... 962261
Jan. 24, 1997 (FI) .......................................... 970303

(51) Int. Cl.$^7$ .................. D21C 9/10; D21C 9/16
(52) U.S. Cl. .................. 162/65; 162/72; 162/76; 162/78
(58) Field of Search .................. 162/76, 72, 78, 162/90, 79, 82, 65

(56) References Cited

U.S. PATENT DOCUMENTS

| 4,044,034 | 8/1977 | Christiansen | 260/404.5 |
| 5,205,907 | * 4/1993 | Fortier | 162/78 |
| 5,431,781 | 7/1995 | Walsh | 162/76 |

FOREIGN PATENT DOCUMENTS

| 0 532 003 A1 | 3/1993 | (EP) . |
| 0 740 015 A1 | 10/1996 | (EP) . |
| 51-2708 | 1/1976 | (JP) . |
| 6-282044 | 7/1994 | (JP) . |
| 7-120899 | 5/1995 | (JP) . |
| 7-261355 | 10/1995 | (JP) . |
| 7-120894 | 12/1995 | (JP) . |
| WO 94/12721 | 6/1994 | (WO) . |
| WO 95/14808 | 6/1995 | (WO) . |

OTHER PUBLICATIONS van Westrenen, J., The synthesis of polyhydroxycarboxylates. Part 6. N–Alkylation of amino compounds by a Michael–type addition with maleate., Recl. Trav. Chim. Pays–Bas., vol. 109 (1990).

* cited by examiner

Primary Examiner—Steve Alvo
(74) Attorney, Agent, or Firm—Morgan & Finnegan, L.L.P.

(57) ABSTRACT

A process for the bleaching of chemical pulp, in which process the pulp is delignified with a peracid and additionally the pulp is chelated in order to bind heavy metals, such as Fe, Mn and/or Cu, into a chelate complex. According to the invention, the chelating is carried out using a chemical which has been selected from a group consisting of N-bis-((1,2-dicarboxy-ethoxy)-ethyl)-amine, N-bis-((1,2-dicarboxy-ethoxy)-ethyl)-aspartic acid and N-tris-((1,2-dicarboxy-ethoxy)-ethyl)-amine, as well as the alkali metal and earth-alkali metal salts thereof, and the peracid and chelating treatments are carried out simultaneously by combining the peracid and the said chelating chemical in the same solution phase. In the bleaching sequence the treatment according to the invention may follow, for example, an ozone delignification and precede an alkaline peroxide step, and in the latter case a magnesium compound, such as $MgSO_4$, may be added to the pulp before the alkali step.

10 Claims, No Drawings

PROCESS FOR THE PERACID BLEACHING OF CHELATED CHEMICAL PULP

The present invention relates to a process for the bleaching of chemical pulp, in which process the pulp is delignified with a peracid and additionally the pulp is chelated in order to bind heavy metals, such as Fe, Mn and/or Cu, into a chelate complex.

In the production of chemical pulp, a cellulose-containing material is cooked with suitable cooking chemicals, and the raw pulp thus obtained is delignified and bleached with oxidizing chemicals. The purpose of the conventional bleaching of chemical pulp is to complete the removal of lignin from the raw pulp obtained from the cook. Chlorine or chlorine dioxide has conventionally been used for bleaching, but recently a shift has increasingly been made to other, replacing bleaching chemicals. The bleaching takes place in a plurality of successive steps, for example so that the first step is an oxygen delignification, whereafter the delignification may be continued by using, for example, ozone, peracetic acid or hydrogen peroxide in acidic or alkaline conditions.

When oxygen-containing bleaching chemicals, such as oxygen, ozone, hydrogen peroxide and peracids, are used, problems are caused by heavy metals present in the pulp; these include in particular iron, manganese and copper, but also, for example, chromium and nickel. These heavy metals enter the raw pulp along with wood, process waters or cooking chemicals, and they catalyze the decomposition of the carbohydrates in the presence of oxygen chemicals, thereby increasing the consumption of the bleaching chemical and deteriorating the quality of the pulp. Furthermore, they cause after-darkening of the pulp. It is possible to remove the heavy metals, for example, by an acid wash preceding the bleaching step, but since the subsequent bleaching step in the bleaching sequence is usually alkaline, an acid wash performed at a low pH will increase the amount of alkali required for the adjustment of the pH. There is the further disadvantage that the acid wash may reduce the strength of the pulp and that earth-alkali metal ions which are regarded as advantageous for bleaching are removed in the wash. Earth-alkali metals, such as magnesium and calcium, stabilize peroxide in peroxide bleaching and protect the carbohydrates of the pulp from decomposition in the oxygen step; for this reason magnesium sulfate is often added to the bleaching steps.

An alternative method for mitigating the disadvantages due to heavy metals is chelating, wherein complexing agents are used as chelating agents. It is assumed that chelating has the advantage over acid wash that calcium and magnesium will better remain in the pulp. Known chelating agents which bind heavy metals include polycarboxylic acids, of which ethylenediaminetetaacetic acid (EDTA) and diethylenetriaminepentaacetic acid (DTPA), and salts thereof, are the ones most commonly used.

The chelating of chemical pulp will in general not succeed satisfactorily in alkaline conditions, since iron forms very poorly soluble compounds by precipitating in the form of hydroxides, oxides and oxyhydroxides. When the pH rises above 7, manganese also begins to bind very strongly to the pulp. For this reason, chelating in bleaching has been carried out as a separate step in acidic conditions. Such a separate chelating step is very effective in binding heavy metals, but it neither bleaches the pulp nor delignifies it; thus it serves only as a preliminary step for the subsequent oxygen chemical step. If the separate chelating step could be replaced by some sufficiently selective delignifying step, for example the kappa number in the cook could be raised owing to the improved delignification and the yield could be improved, or respectively, the delignification could be brought to a further point and higher degrees of brightness could be reached without a reduction of the strength of the pulp.

One delignification process which has been found to be highly selective is based on the use of peracids. In peracid delignification it is possible to use organic or inorganic peracids, of which peracetic acid and Caro's acid are the most commonly used. It has been observed that peracetic acid (PAA) is an especially selective delignification chemical by means of which the strength properties of the pulp can be maintained good. The PAA step is in fact itself not very sensitive to heavy metals, and even moderately high Fe or Mn concentrations do not affect the selectivity of PAA. In the PAA step the iron remains in the form of poorly soluble Fe(III), whereas a considerable amount of manganese dissolves. This released manganese will pass together with the pulp to the subsequent final bleaching with alkaline peroxide, in which manganese has a detrimental effect and before which the pulp must be chelated in order to avoid the said disadvantage. Furthermore, the PAA step removes from the pulp earth-alkali metals, mainly magnesium and calcium, which are useful in further bleaching.

In delignification with peracetic acid, the optimum pH is very close to that (4–6.5) used in the chelating step. However, chelating which binds heavy metals has not been successful in connection with a PAA step, since DTPA and EDTA, the most commonly used chelating agents, form with manganese a complex which decomposes peracetic acid very effectively. Furthermore, if DTPA decomposes in the reactions, large amounts of iron and manganese are left in the pulp; this is detrimental for the subsequent bleaching steps. In the PAA step the final pH is often rather low, approximately 4, in which case large amounts of Mg and Ca dissolve and, as a consequence, the Mg:Mn ratio in the pulp passing to the subsequent step is poor. The wrong metal profile is in general not seen in the pulp properties after the actual PAA steps; the viscosity is at a good level. However, in the subsequent alkaline peroxide step the wrong metal profile causes extra consumption of peroxide and a lowering of the viscosity of the pulp. Thus a separate chelating step between the PAA and peroxide steps has been required; such a step is futile in terms of delignification, but without it the strength of the pulp could be reduced and the consumption of peroxide could increase considerably in the peroxide step, which is the actual bleaching step.

The object of the present invention is to provide a process in which a chelating which binds heavy metals can be combined with peracid delignification, so that the process will be simpler than previously. The process is based on the use of new complexing agents, and it is characterized in that the chelating is carried out using a chemical selected from a group consisting of N-bis-((1,2-dicarboxy-ethoxy)-ethyl)-amine, N-bis-((1,2-dicarboxy-ethoxy)-ethyl)-aspartic acid and N-tris-((1,2-dicarboxy-ethoxy)-ethyl)-amine and their alkali metal salts and earth-alkali metal salts, and that the peracid and chelating treatments are performed simultaneously by combining the peracid and the said chelating chemical in the same solution phase.

The formulae of the four- and six-branch complexing agents (A, B, C) used as chelating agents in the process are:

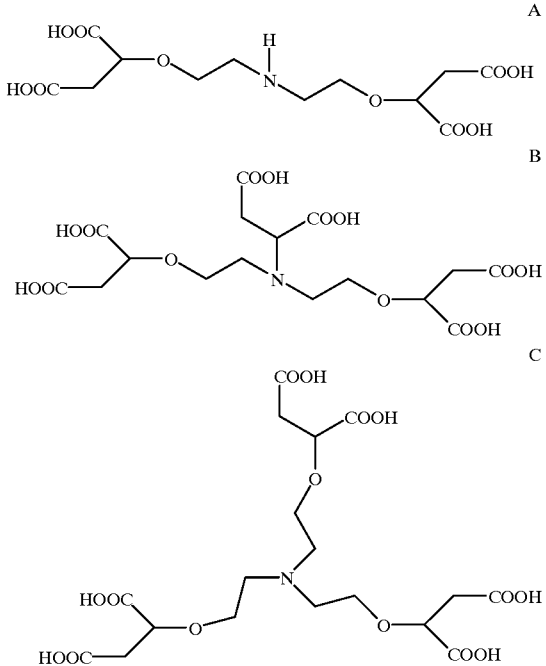

N-bis-[(1,2-dicarboxy-ethoxy)-ethyl]-amine (A) is hereinafter referred to by using the acronym BCEEA, N-bis-[1,2-dicarboxy-ethoxy)-ethyl]-aspartic acid (B) by using the acronym BCEEAA and N-tris-[(1,2-dicarboxy-ethoxy)-ethyl]-amine (C) by using the acronym TCEEA.

The achievement of the invention is that peracid delignification, chelating and bleaching, which previously constituted three separate steps in the bleaching process, can be performed during two steps. As the separate chelating step is eliminated, the resources (e.g. a bleaching tower) required by it can be used, for example, for increasing the retention time in some other bleaching step.

The use of the new chelating agents has the additional advantage that, while they chelate iron and manganese sufficiently effectively, they hardly seem to chelate magnesium and calcium.

The peracid used as the delignification chemical may be peracetic acid, performic acid, perpropionic acid or a longer-chain percarboxylic acid. The peracid may also be monopersulfinic acid (Caro's acid) or a mixture of Caro's acid and a percarboxylic acid, e.g. peracetic acid. Persulfates may also be used as a mixture with any of the above-mentioned peracids. It is also possible to use a combination of a peracid and chlorine dioxide, for example peracetic acid and chlorine dioxide simultaneously. According to the invention, preferred peracids include peracetic acid, Caro's acid, or a mixture thereof. Especially preferably it is peracetic acid, the advantage of which over Caro's acid is that peracetic acid can be purified by distillation and can be stored for relatively long periods, whereas Caro's acid must be used as an equilibrium solution which contains a large amount of unreacted acid. A large amount of unreacted acid complicates pH control.

The process according to the invention can be used advantageously in connection with ozone delignification in which part of the delignification is carried out with a peracid, such as peracetic acid. The process exploits the neutralization step following the ozone step, in which case the metal profile of the pulp can be adjusted so as to be suitable for further bleaching. At the same time part of the delignification work and the removal of the chromophores from the pulp can be left for the peracetic acid and/or chromophores may be removed from the pulp, whereby the further bleaching is facilitated. On the other hand, the strength of the pulp is also improved when part of the delignification is left for a peracid which is more selective than ozone.

In ozone delignification the pH is dropped to a very low level. Thereby the earth-alkali metals present in the pulp may be dissolved. Of the heavy metals, manganese is rather easily removed in an acid treatment, but iron is very poorly soluble. The ozonation is followed by a neutralization step. There is no wash between the steps, and thus the heavy metals may become rebound to the fiber. However, this problem can be avoided by using in this step complexing agents according to the invention, by means of which the heavy metals can be chelated into a soluble form.

It has further been observed that, if the pH of the neutralization step according to the invention, comprising a peracid delignification and chelation, is maintained within a suitable range and magnesium sulfate is added to the step, a suitable metal profile for the pulp is obtained before the subsequent alkaline peroxide step, in which case the viscosity of the pulp will remain considerably good in the further bleaching. The viscosities of pulps treated by a prior-known technique may be of the same order after the ozone and PAA steps, but owing to the wrong metal profile they will drop considerably duting the subsequent alkaline peroxide step.

According to the invention, the pH of the peracid and chelating treatment step can be adjusted advantageously to a range of approximately 4–8. If the PAA delignification is carried out within a pH range of 4–5, PAA is relatively stable and its delignifying effect is at its best. Within a pH range of approximately 6–8, PAA is not equally stable, but respectively it serves, in addition to delignifying, also as a bleaching chemical. Since, owing to the relatively high plice of PAA, it is most profitable to carry out the PAA delignification towards the end of the sequence, preferably immediately before the last alkaline peroxide, PAA can also be used as a bleaching chemical and the actual delignification can be left for the other delignification chemicals, such as oxygen and ozone. A bleaching PAA step may be especially useful when the pulp is difficult to bleach.

There are no limitations on the use of the process in a multistep bleaching sequence; it can be used on a pulp coming directly from the cook, on all oxygen-delignified pulp, or on pulp after any step. The process is especially advantageous for use before alkaline peroxide bleaching.

The process is suitable for use on sulfate pulps and other chemical pulps made from softwood or hardwood or various grasses. The process can also be used for inhibiting after-darkening of bleached pulps.

The invention is illustrated in greater detail with the following examples. It should be pointed out that the mixture of chelating agents BCEEA+BCEEAA according to the invention, used in the examples, contained 18% BCEEA and 34% BCEEAA, the balance being mainly water. The doses (kilograms/metric ton of pulp) in the examples have been calculated for all chelating agents as 100% sodium salts.

PREPARATION EXAMPLE 1

A disodium maleate solution was prepared by dissolving 29.4 g (0.3 mol) of maleic anhydride in 50 ml of water and by adding to the reaction mixture 50 g of a 48% caustic solution (0.6 mol NaOH). During the adding the temperature of the reaction mixture was maintained at 70–90° C. 17 g (0.05 mol) of lanthanum(III) nitrate, La(NO$_3$)$_3$×6 H$_2$O was added to the reaction mixture together with diethanolamine (10.5 g, 0.1 mol). The reaction mixture was stirred at 85° C. under a reflux condenser for 48 h. The reaction mixture was cooled and was rendered acidic (pH 1.8) by means of a concentrated sulfuric acid. Thereafter the reaction mixture was reheated to 60° C., and 10 g of oxalic acid and 50 ml of water were added, the mixture was stirred at 60° C. for 20 minutes, and the La(III) oxalate precipitate formed was removed from the hot solution by filtration. The filtrate was cooled, and any precipitate subsequently formed was removed by filtration. The remaining solution (40 ml), which contained 54% water, was analyzed for organic compounds by means of $^{13}$C NMR spectra and a mass spectrometer as silyl or methyl ester derivatives.

BCEEAA and BCEEA were identified from the $^{13}$C NMR spectrum. The unreacted starting substances were identified on the basis of reference spectra: diethanolamine and maleic acid, as well as oxalic acid which was used for precipitating the catalyst. Malic acid and fumaric acid formed as byproducts of the reaction; these were also identified on the basis of reference spectra.

On the basis of a quantitative $^{13}$C NMR analysis, the composition of the obtained reaction mixture was as follows:

|  | % by weight |
| --- | --- |
| BCEEAA | 18.5 |
| BCEEA | 7.9 |
| diethanolamine | 1.2 |
| maleic acid | 2.2 |
| malic acid | 2.5 |
| oxalic acid | 0.3 |
| fumaric acid | 2.1 |
| water | 54.3 |
| Na$_2$SO$_4$ | 11.0 |

The said analysis and the ascertaining of the molecular structures of the compounds BCEEA and BCEEAA by gas chromatography and mass spectrometry are described in the priority application FI-962261.

In order to isolate the compounds BCEEA and BCEEAA, a sample (13.25 g) of the reaction mixture obtained as described above was pretreated by adding to it 1.16 g of calcium carbonate. Thereupon the sulfate ions present in the sample precipitated as calcium sulfate.

The ion exchange resin used was a strong anion exchange resin (Bio-Rad AG1-X8, 200–400 mesh) in its folmiate form. The sample was eluted through an ion exchange column with an eluent (1000 ml), the formic acid concentration of which was increased gradually so that the formic acid concentration of the eluent ranged from 0 to 2 mol/l. During the run, one hundred samples of 10–20 ml were collected and were analyzed by a liquid chromatograph. BCEEA and BCEEAA were isolated from the fractions. The $^{13}$C NMR spectra and GC-MS spectra of the reaction products were ascertained by comparing the spectrum data for the purified and isolated reaction products with the spectrum data for the reaction products identified from the reaction mixture. The spectrum data of the purified BCEEA and BCEEAA were found to be identical with those obtained from the reaction mixture.

PREPARATION EXAMPLE 2

A magnesium maleate solution was prepared by dissolving 29.4 g (0.3 mol) of maleic anhydride in 50 ml of water and by adding to the reaction mixture 35.0 g of magnesium hydroxide (0.3 mol Mg(OH)$_2$) slurried in 70 ml of water. During the adding the temperature of the reaction mixture was maintained at 70–90° C. 17 g (0.05 mol) of lanthanum (III) nitrate, La(NO$_3$)$_3$×6 H$_2$O was added to the reaction mixture together with diethanolamine (10.5 g, 0.1 mol). The pH of the reaction mixture was adjusted to a pH value of 11 by an addition of a 48% sodium hydroxide solution. The reaction mixture was stirred at 85° C. under a reflux condenser for 10 hours. The reaction mixture was cooled and was rendered acidic (pH 1.8) by means of a concentrated sulfuric acid. Thereafter the reaction mixture was reheated to 60° C., and 10 g of oxalic acid and 50 ml of water were added, the mixture was stirred at 60° C. for 20 minutes, and the formed precipitate was removed from the hot solution by filtration. The filtrate was cooled and any precipitate subsequently formed was removed by filtration. The remaining solution (42 ml), which contained 54% water, was analyzed for organic compounds by means of $^{13}$C NMR spectra and mass spectrometer as silyl or methyl ester derivatives.

BCEEAA and BCEEA were identified from the $^{13}$C NMR spectra. The unreacted starting substances were identified on the basis of reference spectra: diethanolamine and maleic acid. Malic acid and fumaric acid formed as byproducts of the reaction; these were also identified on the basis of reference spectra.

The organic compound composition of the reaction product was as follows on the basis of a quantitative $^{13}$C NMR analysis:

|  | % by weight |
| --- | --- |
| BCEEAA | 13.8 |
| BCEEA | 4.5 |
| diethanolamine | 7.5 |
| maleic acid | 2.3 |
| malic acid | 1.3 |
| fumaric acid | 0.3 |

PREPARATION EXAMPLE 3

TCEEA was prepared by the method described in Example 1 by using triethanolamine (1.0 mol) and maleic anhydride (3.4 mol) as the starting substances.

TCEEA was identified from the $^{13}$C NMR spectrum. The unreacted starting substances were identified on the basis of reference spectra: triethanolamine and maleic acid, as well as oxalic acid used for precipitating the catalyst. Malic acid and fumaric acid formed as byproducts of the reaction; these were also identified on the basis of reference spectra.

On the basis of a quantitative $^{13}$C NMR analysis, the composition of the reaction product was as follows:

|  | molar % |
| --- | --- |
| TCEEA | 46.3 |
| triethanolamine | 18.5 |
| maleic acid | 11.5 |
| fumaric acid | 3.2 |
| malic acid | 13.5 |
| oxalic acid | 6.6 |

EXAMPLE 1

The rate of decomposition of PAA in the presence of manganese was measured by using various chelating agents at a pH of approximately 4 and a temperature of 60° C. Initially the PAA concentration was 2 g/l. The results are shown in Table 1.

TABLE 1

| Chelating agent | Mn, ppm | Residual PAA, % | | | |
|---|---|---|---|---|---|
| | ppm | 5 min | 15 min | 30 min | 60 min |
| No chelating agent | | 0.4 | 93.1 | 93.0 | 91.2 | 87.4 |
| DTPA | 140 | 0.4 | 13.5 | 5.5 | 0.0 | 0.0 |
| EDTA | 140 | 0.4 | 8.1 | 4.3 | 3.3 | 0.0 |
| BCEEA + BCEEAA | 140 | 0.4 | 99.9 | 97.8 | 98.1 | 95.8 |

The table shows that Mn alone does not decompose PAA very rapidly. DTPA and EDTA complexes decompose it very effectively. On the other hand, the results show the BCEEA+ BCEEAA mixture according to the invention even improves the stability of PAA in the presence of manganese.

EXAMPLE 2

The PAA step of the bleaching of a softwood sulfate pulp having a viscosity of 710 dm$^3$/kg, a kappa number of 6.7 and a brightness of 79.7% ISO was performed at two different pH values with and without magnesium sulfate by using various chelating agents. The pulp was first chelated as well as possible (chelating agent 2 kg/tp of DTPA, temperature 75° C., time 60 min, pH 5.5), whereafter 4 ppm of Mn (=4 g of Mn/metric ton of dry pulp) was added to the PAA step. The addition was made in order that the effect of the chelating agents on the PAA conditions would show clearly. In practice pulps often contain more Mn, unless they are separately chelated before the PAA step. Furthermore, in the PAA step more heavy metals are released from the pulp and would require separate chelation. The PAA step was followed by an alkaline peroxide step.

From the results, which are shown in Table 2, it is observed that the elevated final pH (initial pH 7 and final pH approximately 5) yields a clearly better viscosity than does the lower pH (improvement of the order of approximately 100 dm$^3$/kg). At the higher pH, a viscosity approximately 40 dm$^3$/kg higher is obtained by means of an addition of magnesium sulfate. The mixture of BCEEA and BCEEAA was the best of the chelating agents. At the lower pH the effect of magnesium sulfate was insignificant, and even with the use of chelating agents the improvement in the viscosity was only of the order of 30 dm$^3$/kg. It is also to be noted that the viscosities after the PAA step were for all approximately of the same order (700–730 dm$^3$/kg). However, there are large differences (520–700 dm$^3$/kg) in the viscosities after the subsequent peroxide step; these are due to PAA steps performed in different ways.

EXAMPLE 3

The tests measured the combined effect of magnesium sulfate and chelating agents when iron and manganese had been added to the PAA step. The results are shown in Table 3.

Tests 1 and 2 represent the worst and the best combinations when there was Fe 8 ppm and Mn 4 ppm (calculated per dry pulp) in the PAA step. The difference between the viscosities is approximately 250 dm$^3$/kg and between the peroxide consumptions more than 16 kg/metric ton of pulp. In tests 3 and 4, a comparison was made between DTPA and the BCEEA and BCEEAA mixture when the final pH was approximately 4, in the presence of MgSO$_4$ BCEEA+ BCEEAA yields a viscosity improvement of an order of only approximately 30 dm$^3$/kg and a peroxide consumption 4 kg/tp smaller. Tests 5–7 compared different chelating agents at an elevated pH when there was 8 ppm of iron in the PAA step. The use of chelating agents improves the viscosity by approximately 100–140 dm$^3$/kg, while the consumption of peroxide is lowered by 4–8 kg/tp. This example, also, shows how the viscosities after the PAA step are substantially of the same order (except Test 1, in which it is clearly lower), but after the peroxide step the difference becomes considerably large.

EXAMPLE 4

In the above examples, rather large PAA and peroxide doses were used, whereby an ISO brightness of 88% was reached in almost all cases. In this example, a pulp having a viscosity of 710 dm$^3$/kg, a kappa number of 6.7, and a brightness of 79.7% ISO was chelated (2 kg/tp DTPA, temperature 75° C., time 60 min, pH 5.5), and thereafter the pulp was delignified using a PAA dose of 12 kg and a peroxide dose of 10 kg. With a smaller PAA dose the initial pH may be approximately 6, in which case the final pH will be at a suitable level (final pH approximately 5). 8 ppm FE and 4 ppm Mn (calculated per dry pulp) were added to the PAA step. The results, which are presented in Table 4, show that MgSO$_4$ improves the viscosity by approximately 20 dm$^3$/kg, while the consumption of peroxide is reduced by approximately the same amount. The BCEEA+BCEEAA mixture yields a viscosity approximately 30 dm$^3$/kg higher than does DTPA. In neither case there is left a PAA residue, since the dose was so small that all of it was consumed. However, when DTPA was used, PAA had decomposed to such a degree that the kappa number remained higher. This is shown in the final brightness and the kappa number.

EXAMPLE 5

An oxygen-delignified softwood sulfate pulp having after the oxygen step a kappa number of 7.9, a viscosity of 784 dm$^3$/kg and a brightness of 45% ISO was bleached using a sequence of -Q-EOP-PAA-PO. In the PAA step, magnesium sulfate was used as a stabilizer with the mixture BCEEA+ BCEEAA, with DTPA, and without a chelating agent. The results are shown in Table 5. The results show that BCEEA+ BCEEAA together with magnesium sulfate yielded clearly the highest viscosity and the lowest peroxide consumption in the PO step. On the other hand, after the actual PAA step the viscosity differences were small (except for DTPA, with which it was clearly lowered).

EXAMPLE 6

The raw material used in the example was a softwood sulfate pulp pretreated by chelation before the ozone(Z) step, in which case after chelation the amount of free heavy metal ions present in the pulp was insignificant. The initial kappa number of the ozone step was 6.7, the viscosity was 947 dm$^3$/kg, and the brightness 51.7% ISO. From the ozone step the pulp was transferred, without a wash, to the PAA step. During the Z and PAA delignification, however, detrimental heavy metal ions are released from the pulp, and in the subsequent alkaline peroxide step they have a disadvantageous effect on peroxide consumption and pulp quality.

As is evident from Table 6 showing the results, clear advantages are gained with the use of a mixture of BCEEA and BCEEAA in the PAA step in terms of both PAA delignification and the functioning of the subsequent alkaline peroxide step (cf. DTPA). An even clearer difference is viscosity value 200–280 dm³/kg higher, and compared with DTPA the difference was 200–50 dm3/kg.

TABLE 2

| Test batch | 1 | 2 | 3 | 4 | 5 | 6 | 7 | 8 | 9 | 10 | 114 | 12 | 13 | 14 |
|---|---|---|---|---|---|---|---|---|---|---|---|---|---|---|
| PAA | | | | | | | | | | | | | | |
| Time, min | 90 | 90 | 90 | 90 | 90 | 90 | 90 | 90 | 90 | 90 | 90 | 90 | 90 | 90 |
| Temperature, °C. | 80 | 80 | 80 | 80 | 80 | 80 | 80 | 80 | 80 | 80 | 80 | 80 | 80 | 80 |
| Consistency, % | 12 | 12 | 12 | 12 | 12 | 12 | 12 | 12 | 12 | 12 | 12 | 12 | 12 | 12 |
| pH, initial | 7 | 7 | 7 | 7 | 7 | 7 | 7 | 5 | 5 | 5 | 5 | 5 | 5 | 5 |
| pH, final | 5.4 | 5.4 | 5.6 | 5.1 | 5.3 | 5.6 | 5.2 | 4.5 | 3.9 | 4.3 | 3.9 | 4.2 | 4.2 | 4 |
| PAA, kg/tp | 20 | 20 | 20 | 20 | 20 | 20 | 20 | 20 | 20 | 20 | 20 | 20 | 20 | 20 |
| $MgSO_4$, kg/tp | — | 1 | 1 | 1 | — | — | — | — | 1 | 1 | 1 | — | — | — |
| Mn, ppm | — | 4 | 4 | 4 | 4 | 4 | 4 | — | 4 | 4 | 4 | 4 | 4 | 4 |
| DTPA, kg/tp | — | — | 2 | — | — | 2 | — | — | — | 2 | — | — | 2 | — |
| BCEEA + BCEEAA, kg/tp | — | — | — | 2 | — | — | — | — | — | — | 2 | — | — | 2 |
| Residual $H_2O_2$, kg/tp | 1.4 | 0.2 | 0.6 | 0.8 | 0.3 | 0.8 | 0.9 | 0.8 | 0.5 | 0.7 | 1 | 0.3 | 0.8 | 1.1 |
| Residual PAA, kg/tp | 0.5 | 1.3 | 0.4 | 0.5 | 0.3 | 0.4 | 0.6 | 7.4 | 5.9 | 0.4 | 6.6 | 3.1 | 0.7 | 7 |
| Kappa | 2.8 | 2.2 | 3.5 | 2.6 | 3.2 | 3.4 | 2.7 | 2.2 | 2.1 | 3.2 | 2.2 | 2.1 | 2.7 | 2.2 |
| Viscosity, dm³/kg | 731 | 725 | 688 | 726 | 728 | 699 | 732 | 737 | 720 | 667 | 717 | 708 | 620 | 717 |
| Brightness, % ISO | 85.7 | 85.8 | 84.7 | 85.6 | 84.9 | 85.2 | 85.9 | 84 | 83.7 | 82.3 | 83.8 | 83.8 | 82.9 | 83.6 |
| Peroxide | ↓ | ↓ | ↓ | ↓ | ↓ | ↓ | ↓ | ↓ | ↓ | ↓ | ↓ | ↓ | ↓ | ↓ |
| Time, min. | 90 | 90 | 90 | 90 | 90 | 90 | 90 | 90 | 90 | 90 | 90 | 90 | 90 | 90 |
| Temperature, °C. | 90 | 90 | 90 | 90 | 90 | 90 | 90 | 90 | 90 | 90 | 90 | 90 | 90 | 90 |
| Consistency, % | 12 | 12 | 12 | 12 | 12 | 12 | 12 | 12 | 12 | 12 | 12 | 12 | 12 | 12 |
| pH, initial | 10.5 | 10.5 | 10.5 | 10.5 | 10.5 | 10.5 | 10.5 | 10.5 | 10.5 | 10.5 | 10.5 | 10.5 | 10.5 | 10.5 |
| pH, final | 10.5 | 10.7 | 10.4 | 10.3 | 10.5 | 10.4 | 10.4 | 10.4 | 10.4 | 10.4 | 10.5 | 10.5 | 10.4 | 10.5 |
| $H_2O_2$, kg/tp | 20 | 20 | 20 | 20 | 20 | 20 | 20 | 20 | 20 | 20 | 20 | 20 | 20 | 20 |
| NaOH, kg/tp | 12 | 12 | 12 | 12 | 12 | 12 | 12 | 12 | 12 | 12 | 12 | 12 | 12 | 12 |
| Residual $H_2O_2$, kg/tp | 12.1 | 3.2 | 13.1 | 16.9 | 10.2 | 9.5 | 16.2 | 10.1 | 4.6 | 8.9 | 7.1 | 4.5 | 11 | 10 |
| Residual NaOH, kg/tp | 7.7 | 7.3 | 7.7 | 8.4 | 8 | 7.7 | 8.2 | 6.3 | 6 | 5.4 | 6 | 5.3 | 6.2 | 7.2 |
| Kappa | 2.3 | 1.7 | 3 | 2.2 | 2.6 | 2.9 | 2.3 | 1.7 | 1.5 | 2.6 | 1.6 | 1.5 | 2.1 | 0.9 |
| Viscosity, dm³/kg | 593 | 638 | 624 | 698 | 656 | 585 | 662 | 573 | 540 | 523 | 545 | 540 | 571 | 576 |
| Brightness, % ISO | 88.2 | 89.1 | 88.4 | 88.87 | 88.8 | 88.8 | 88.9 | 88.5 | 89 | 87.9 | 89.1 | 89.4 | 88.4 | 88.7 | observed when the results are compared with a Z/PAA-P sequence without a complexing agent.

The table shows that 8 g of Fe/metric ton of pulp and 4 g of Mn/metric ton of pulp were added to the Z step. The additions were made in order that the differences between the different treatment methods would show sufficiently clearly. In the presence of heavy metals, an addition of the BCEEA+BCEEAA mixture to the PAA step improves the result of the Z/PAA step considerably as compared with the reference in which no complexing agent is used. The said mixture also yields a clearly better result than does DTPA if the pulp quality and chemical consumption achieved with the sequence Z/PAA-P is compared in Z/PAA and P steps. In the final viscosities the difference between DTPA and the BCEEA+BCEEAA mixture was small, but with BCEEA+BCEEAA the brightness was higher and the consumption of peroxide was considerably small.

EXAMPLE 7

A softwood sulfate pulp which had been oxygen delignified and had a kappa number of 9.7, a viscosity of 775 dm³/kg and a brightness of 49.3% ISO was bleached using the sequence PAA-P-PAA-P. The results are shown in Table 7. The results show that a PAA+Q treatment in which the initial pH is 5 yields a clearly lower viscosity than does a treatment in which the initial pH is 7. Regardless of the pH, DTPA yields lower viscosities (Tests 3 and 4) than does TCEEA and a mixture of BCEEA and BCEEAA, but nevertheless somewhat higher than without an addition of a chelating agent. As compared with a chelating agent-free PAA treatment, BCEEA+BCEEAA at its best yielded a

TABLE 3

| Test | | 1 | 2 | 3 | 4 | 5 | 6 | 7 |
|---|---|---|---|---|---|---|---|---|
| PAA | | | | | | | | |
| Time | min. | 90 | 90 | 90 | 90 | 90 | 90 | 90 |
| Temperature | °C. | 80 | 80 | 80 | 80 | 80 | 80 | 80 |
| Consistency | % | 12 | 12 | 12 | 12 | 12 | 12 | 12 |
| pH initial | | 5 | 7 | 5 | 5 | 7 | 7 | 7 |
| pH final | | 4.2 | 5.3 | 4.3 | 4.3 | 5.4 | 5.5 | 5.6 |
| PAA | kg/tp | 20 | 20 | 20 | 20 | 20 | 20 | 20 |
| $MgSO_4$ | kg/tp | — | 1 | 1 | 1 | — | — | — |
| Fe | ppm | 8 | 8 | 8 | 8 | 8 | 8 | 8 |
| Mn | ppm | 4 | 4 | — | — | — | — | — |
| DTPA | kg/tp | — | — | 2 | — | — | 2 | — |
| BCEEA + BCEEAA | kg/tp | — | 2 | — | 2 | — | — | 2 |
| Kappa | | 1.8 | 2.8 | 2.2 | 2.3 | 2.6 | 2.8 | 2.8 |
| Viscosity | dm³/kg | 647 | 707 | 719 | 725 | 707 | 718 | 715 |
| Brightness | % ISO | 82.8 | 85.1 | 84.1 | 84.5 | 84.3 | 84.6 | 84.6 |
| Peroxide | | ↓ | ↓ | ↓ | ↓ | ↓ | ↓ | ↓ |
| Time | min. | 90 | 90 | 90 | 90 | 90 | 90 | 90 |
| Temperature | °C. | 90 | 90 | 90 | 90 | 90 | 90 | 90 |
| Consistency | % | 12 | 12 | 12 | 12 | 12 | 12 | 12 |
| pH initial | | 10.5 | 10.5 | 10.4 | 10.4 | 10.5 | 10.5 | 10.5 |
| pH final | | 10.2 | 10.4 | 10.5 | 10.5 | 10.4 | 10.4 | 10.4 |
| $H_2O_2$ | kg/tp | 20 | 20 | 20 | 20 | 20 | 20 | 20 |
| Residual $H_2O_2$ | kg/tp | 0.1 | 16.3 | 0.9 | 4.1 | 4.5 | 8.4 | 11.6 |
| Kappa | | 1.3 | 2.4 | 1.5 | 1.5 | 2.2 | 2.6 | 2.4 |
| Viscosity | dm³/kg | 415 | 673 | 462 | 492 | 455 | 546 | 577 |
| Brightness | % ISO | 89 | 88.9 | 88.8 | 88.8 | 88.8 | 88.7 | 88.7 |

TABLE 4

| Test | | 1 | 2 | 3 | 4 |
|---|---|---|---|---|---|
| PAA | | | | | |
| Time | min. | 90 | 90 | 90 | 90 |
| Temperature | °C. | 80 | 80 | 80 | 80 |
| Consistency | % | 12 | 12 | 12 | 12 |
| pH initial | | 6 | 6 | 6.2 | 6.2 |
| pH final | | 5 | 5 | 5.2 | 5.2 |
| PAA | kg/tp | 12 | 12 | 12 | 12 |
| $MgSO_4$ | kg/tp | 1 | — | 1 | — |
| Fe | ppm | 8 | 8 | 8 | 8 |
| Mn | ppm | 4 | 4 | 4 | 4 |
| Chelating agent | | BCEEA + BCEEAA | BCEEA + BCEEAA | DTPA | DTPA |
| | kg/tp | 2 | 2 | 2 | 2 |
| Residual $H_2O_2$ | kg/tp | 0.4 | 0.6 | 0.7 | 0.6 |
| Residual PAA | kg/tp | 0.4 | 0.5 | 0.5 | 0.4 |
| Kappa | | 3 | 3 | 4 | 3.9 |
| Viscosity | $dm^3$/kg | 720 | 734 | 716 | 720 |
| Brightness | % ISO | 84.6 | 84.6 | 84.6 | 84.6 |
| Peroxide | | ↓ | ↓ | ↓ | ↓ |
| Time | min. | 90 | 90 | 90 | 90 |
| Temperature | °C. | 90 | 90 | 90 | 90 |
| Consistency | | 12 | 12 | 12 | 12 |
| pH initial | | 10.4 | 10.4 | 10.4 | 10.4 |
| pH final | | 10.1 | 10.3 | 10.2 | 10.3 |
| $H_2O_2$ | kg/tp | 10 | 10 | 10 | 10 |
| NaOH | kg/tp | 7 | 7 | 7 | 7 |
| Residual $H_2O_2$ | kg/tp | 8.4 | 6.5 | 6.3 | 5.0 |
| Residual NaOH | kg/tp | 3.9 | 3.6 | 3.6 | 3.9 |
| Kappa | | 2.7 | 2.6 | 3.4 | 3.5 |
| Viscosity | $dm^3$/kg | 697 | 668 | 669 | 649 |
| Brightness | % ISO | 88.0 | 88.0 | 87.6 | 87.7 |

TABLE 5

| Q | | |
|---|---|---|
| Time | min | 60 |
| Temperature | °C. | 80 |
| Consistency | % | 15 |
| pH | | 5.4 |
| DTPA | kg/tp | 2 |
| $H_2SO_4$ | kg/tp | 3 |

↓

| EOP | | |
|---|---|---|
| Time | min | 120 |
| Temperature | °C. | 87 |
| Consistency | % | 15 |
| pH | | 10.4 |
| NaOH | kg/tp | 9 |
| $H_2SO_4$ | kg/tp | 10 |
| $MgSO_4$ | kg/tp | 1 |
| $O_2$ | bar | 4 |
| Residual $H_2O_2$ | kg/tp | 2.2 |
| Residual NaOH | kg/tp | 3 |
| Kappa | | 4.9 |
| Viscosity | $dm^3$/kg | 764 |
| Brightness | % ISO | 67.3 |

TABLE 5-continued

↙ ↓ ↘

| PAA | | | | |
|---|---|---|---|---|
| Time | min | 60 | 60 | 60 |
| Temperature | °C. | 87 | 87 | 87 |
| Consistency | % | 15 | 15 | 15 |
| pH | | 5 | 4.6 | 5.1 |
| DTPA | kg/tp | - | - | 1 |
| $MgSO_4$ | kg/tp | 1 | 1 | 1 |
| BCEEA + BCEEAA | kg/tp | - | 1 | - |
| PAA | kg/tp | 10 | 10 | 10 |
| Residual $H_2O_2$ | kg/tp | 0.5 | 0.6 | 0.6 |
| Residual NaOH | kg/tp | 4.7 | 3.3 | 1.6 |
| Kappa | | 3 | 3 | 3.2 |
| Viscosity | $dm^3$/kg | 749 | 754 | 699 |
| Brightness | % ISO | 73.2 | 73 | 73.7 |

↓ ↓ ↓

| PO | | | | |
|---|---|---|---|---|
| Time | min | 150 | 150 | 150 |
| Temperature | °C. | 97 | 97 | 97 |
| Consistency | % | 15 | 15 | 15 |
| pH | | 9.4 | 9.9 | 9.7 |
| $H_2O_2$ | kg/tp | 15 | 15 | 15 |
| NaOH | kg/tp | 8 | 8 | 8 |
| $O_2$ | bar | 6 | 6 | 6 |
| $MgSO_4$ | kg/tp | 1 | 1 | 1 |
| Residual $H_2O_2$ | kg/tp | 1.3 | 4.5 | 2.6 |
| Residual NaOH | kg/tp | 1 | 1.8 | 1 |
| Kappa | | 1.6 | 1.5 | 1.6 |
| Viscosity | $dm^3$/kg | 561 | 643 | 574 |
| Brightness | % ISO | 85.8 | 86.9 | 86.2 |

TABLE 6

| Z | | | | |
|---|---|---|---|---|
| Test | | 1 | 2 | 3 |
| Time | min | 2+2 | 2+2 | 2+2 |
| Temperature | °C. | 55 | 55 | 55 |
| Consistency | % | 12 | 12 | 12 |
| pH | initial | 3.5 | 3.5 | 3.5 |
| pH | final | 3.2 | 3.5 | 3.4 |
| Fe+Mn | final | 8+4 | 8+4 | 8+4 |
| $O_3$ | kg/tp | 1.5+1.5 | 1.5+1.5 | 1.5+1.5 |

↘ ↘ ↘

| PAA | | | | | | | |
|---|---|---|---|---|---|---|---|
| Test | | 1a | 1b | 2a | 2b | 3a | 3b |
| Time | min | 30 | 30 | 30 | 30 | 30 | 30 |
| Temperature | °C. | 70 | 70 | 70 | 70 | 70 | 70 |
| Consistency | % | 10 | 10 | 10 | 10 | 10 | 10 |
| pH | initial | 6 | 6 | 6 | 6 | 6 | 6 |
| pH | kg/tp | 5.6 | 5.6 | 5.6 | 5.6 | 5.6 | 5.6 |
| DPTA | kg/tp | 2 | 2 | - | - | - | - |
| $MgSO_4$ | kg/tp | - | 1 | - | 1 | - | 1 |
| Peracetic acid | kg/tp | 5 | 5 | 5 | 5 | 5 | 5 |
| BCEEA + BCEEAA | kg/tp | - | - | 2 | 2 | - | - |
| NaOH | kg/tp | 6 | 6 | 6 | 6 | 6 | 6 |
| Residual PAA | kg/tp | 0.7 | 0.7 | 0.7 | 0.7 | 0.7 | 0.7 |
| Residual $H_2O_2$ | kg/tp | 0.7 | 0.7 | 1.1 | 1.3 | 1.1 | 1 |
| Kappa | | 3.3 | 3.1 | 3.1 | - | - | - |
| Viscosity | dm³/kg | 656 | 658 | 676 | 667 | 653 | 665 |
| Brightness | % ISO | 84.1 | 84.4 | 84.2 | 84.3 | 84.2 | 83.7 |

TABLE 6-continued

| P | | ↓ | ↓ | ↓ | ↓ | ↓ | ↓ |
|---|---|---|---|---|---|---|---|
| Time | min | 90 | 90 | 90 | 90 | 90 | 90 |
| Temperature | °C. | 90 | 90 | 90 | 90 | 90 | 90 |
| Consistency | % | 12 | 12 | 12 | 12 | 12 | 12 |
| pH | alussa | 10.5 | 10.5 | 10.5 | 10.5 | 10.5 | 10.5 |
| pH | lopussa | 10.4 | 10.4 | 10.4 | 10.3 | 10.4 | 10.3 |
| $H_2O_2$ | kg/tp | 10 | 10 | 10 | 10 | 10 | 10 |
| NaOH | kg/tp | 8 | 8 | 8 | 8 | 8 | 8 |
| Residual $H_2O_2$ | kg/tp | 6.9 | 7.2 | 8.6 | 8.9 | 1.3 | 2 |
| Residual NAOH | kg/tp | 4.5 | 4.8 | 4.6 | 4.5 | 4.2 | 4 |
| Kappa | | 2.8 | 2.8 | 2.6 | 2.6 | 2.5 | 2.5 |
| Viscosity | dm³/kg | 636 | 631 | 644 | 640 | 617 | 615 |
| Brightness | % ISO | 87.6 | 87.7 | 88.1 | 88.2 | 87.9 | 87.9 |

TABLE 7

| Test | | 1 | 2 | 3 | 4 | 5 | 6 | 7 | 8 |
|---|---|---|---|---|---|---|---|---|---|
| PAA | | | | | | | | | |
| Time | min | 60 | 60 | 60 | 60 | 60 | 60 | 60 | 60 |
| Temperature | °C. | 80 | 80 | 80 | 80 | 80 | 80 | 80 | 80 |
| Consistency | % | 12 | 12 | 12 | 12 | 12 | 12 | 12 | 12 |
| pH | initial | 5 | 7–7.5 | 5 | 7–7.5 | 5 | 7–7.5 | 5 | 7–7.5 |
| pH | final | 4.3 | 6 | 4.4 | 5.9 | 4.4 | 6.1 | 4.5 | 5.9 |
| Chelating agent | | — | — | DTPA | DTPA | TCEEA | TCEEA | BCEEA + BCEEAA | BCEEA + BCEEAA |
| Dose | kg/tp | — | — | 2 | 2 | 2 | 2 | 2 | 2 |
| PAA | kg/tp | 10 | 10 | 10 | 10 | 10 | 10 | 10 | 10 |
| Residual $H_2O_2$ | kg/tp | 0.4 | 0.5 | 0.3 | 0.7 | 0.4 | 0.5 | 0.4 | 0.6 |
| ResidualPAA | kg/tp | 1.9 | 0.7 | 1.7 | 0.5 | 2 | 0.5 | 1.2 | 0.7 |
| Kappa | | 6.8 | 6.9 | 7.3 | 6.6 | 7.4 | 7.3 | 6.7 | 6.8 |
| P | | ↓ | ↓ | ↓ | ↓ | ↓ | ↓ | ↓ | ↓ |
| Time | min | 90 | 90 | 90 | 90 | 90 | 90 | 90 | 90 |
| Temperature | °C. | 90 | 90 | 90 | 90 | 90 | 90 | 90 | 90 |
| Consistency | % | 12 | 12 | 12 | 12 | 12 | 12 | 12 | 12 |
| pH | initial | 10.4 | 10.4 | 10.4 | 10.4 | 10.4 | 10.4 | 10.4 | 10.4 |
| pH | final | 10.2 | 10.2 | 10.1 | 10.2 | 10.1 | 10.1 | 10.1 | 10.1 |
| $H_2O_2$ | kg/tp | 8 | 8 | 8 | 8 | 8 | 8 | 8 | 8 |
| NaOH | kg/tp | 10 | 7 | 9.5 | 8 | 9.5 | 7 | 9 | 7.5 |
| Residual $H_2O_2$ | kg/tp | 4.8 | 5 | 4.4 | 4.9 | 4.5 | 5.4 | 4.8 | 5.5 |
| Residual NaOH | kg/tp | 3.1 | 3.2 | 2.6 | 2.8 | 2.7 | 3.1 | 2.9 | 3.3 |
| Kappa | | 4.6 | 5.3 | 5.1 | 5.2 | 5.2 | 5.9 | 4.6 | 5.1 |
| Viscosity | dm³/kg | 747 | 768 | 755 | 759 | 747 | 768 | 757 | 764 |
| Brightness | % ISO | 74.7 | 76.4 | 73.8 | 76 | 73.6 | 75.4 | 75.5 | 76.5 |
| PAA | | ↓ | ↓ | ↓ | ↓ | ↓ | ↓ | ↓ | ↓ |
| Time | min | 60 | 60 | 60 | 60 | 60 | 60 | 60 | 60 |
| Temperature | °C. | 80 | 80 | 80 | 80 | 80 | 80 | 80 | 80 |
| Consistency | % | 12 | 12 | 12 | 12 | 12 | 12 | 12 | 12 |
| pH | initial | 5 | 7–7.5 | 5 | 7–7.5 | 5 | 7–7.5 | 5 | 7–7.5 |
| pH | final | 4.5 | 6 | 4.7 | 6.2 | 4.7 | 6.1 | 4.9 | 6.2 |

TABLE 7-continued

| Test | | 1 | 2 | 3 | 4 | 5 | 6 | 7 | 8 |
|---|---|---|---|---|---|---|---|---|---|
| Chelating agent | | — | — | DTPA | DTPA | TCEEA | TCEEA | BCEEA + BCEEAA | BCEEA + BCEEAA |
| Dose | kg/tp | — | — | 2 | 2 | 2 | 2 | 2 | 2 |
| PAA | kg/tp | 10 | 10 | 10 | 10 | 10 | 10 | 10 | 10 |
| Residual $H_2O_2$ | kg/tp | 0.6 | 0.6 | 0.5 | 2.2 | 0.5 | 0.7 | 0.8 | 1.1 |
| Residual PAA | kg/tp | 4.4 | 0.8 | 6.2 | 0.5 | 4.2 | 0.5 | 3.4 | 1.1 |
| Kappa | | 3.1 | 3.9 | 4.1 | 4.1 | 4.1 | 4.5 | 3.5 | 3.9 |
| P | | ↓ | ↓ | ↓ | ↓ | ↓ | ↓ | ↓ | ↓ |
| Time | min | 180 | 180 | 180 | 180 | 180 | 180 | 180 | 180 |
| Temperature | °C. | 90 | 90 | 90 | 90 | 90 | 90 | 90 | 90 |
| Consistency | % | 12 | 12 | 12 | 12 | 12 | 12 | 12 | 12 |
| pH | initial | 10.4 | 10.4 | 10.4 | 10.4 | 10.4 | 10.4 | 10.4 | 10.4 |
| pH | final | 9.9 | 10.1 | 10 | 10.1 | 10.2 | 10.2 | 10.1 | 10.1 |
| $H_2O_2$ | kg/tp | 20 | 20 | 20 | 20 | 20 | 20 | 20 | 20 |
| NaOH | kg/tp | 13 | 11 | 13 | 12 | 13 | 11 | 13 | 11 |
| Residual $H_2O_2$ | kg/tp | 0.3 | 5.6 | 3.4 | 9.6 | 8.5 | 12.8 | 12.9 | 13.4 |
| Residual NaOH | kg/tp | 2 | 3.5 | 3.4 | 6.1 | 4.1 | 5.6 | 5.7 | 5.6 |
| Kappa | | 1.5 | 2.4 | 2.2 | 2.9 | 2.3 | 3 | 2.1 | 2.6 |
| Viscosity | $dm^3/kg$ | 426 | 515 | 503 | 648 | 585 | 675 | 656 | 708 |
| Brightness | % ISO | 87.4 | 87.7 | 86.2 | 86.8 | 86.8 | 86.9 | 87.5 | 87.4 |

What is claimed is:

1. A process for the bleaching of chemical pulp, in which process the pulp is delignified with a peracid and additionally the pulp is chelated in order to bind heavy metals selected from the group consisting of Cr, Ni, Fe, Mn and Cu, into a chelate complex, wherein the chelating is carried out using a chemical selected from the group consisting of N-bis-((1,2-dicarboxy-ethoxy)-ethly)-amine, N-bis-((1,2-dicarboxy-ethoxy)-ethyl)-aspartic acid and N-tris-((1,2-dicarboxy-ethoxy)-ethyl)-amine, as well as the alkali metal and earth-alkali metal salts thereof, and that the peracid and chelating treatments are carried out simultaneously by combining the peracid and the chelating chemical in the same solution phase.

2. A process according to claim 1, wherein the peracid is peracetic acid, Caro's acid, or a mixture thereof.

3. A process according to claim 2, wherein the peracid is peracetic acid.

4. A process according to claim 1, wherein the combined peracid and chelating treatment of the pulp follows in the bleaching process an ozone treatment step.

5. A process according to claim 1, wherein the combined peracid and chelating treatment of the pulp is followed by an alkaline peroxide treatment step.

6. A process according to claim 5, wherein, in connection with the peracid and chelating treatment, a magnesium compound is added to the pulp.

7. A process according to claim 6 wherein the pH of the peracid and chelating treatment step is adjusted to a range of approximately 4–8, and that this step is followed by an alkaline peroxide step.

8. A process according to claim 6 wherein the magnesium compound is magnesium sulfate.

9. A process according to claim 5 wherein the pH of the peracid and chelating treatment step is adjusted to a range of approximately 4–8, and that this step is followed by an alkaline peroxide step.

10. A process according to claim 1, wherein the pulp is a sulfate pulp obtained from hardwood or softwood.

* * * * *